US00PP19312P3

(12) United States Plant Patent
McLaren

(10) Patent No.: US PP19,312 P3
(45) Date of Patent: Oct. 7, 2008

(54) *APPLE TREE* NAMED 'PB-148'

(50) Latin Name: *Malus pumila Mill*
Varietal Denomination: PB-148

(75) Inventor: John McLaren, Cromwell (NZ)

(73) Assignee: Nevis Fruit Company Ltd. (NZ)

( * ) Notice: Subject to any disclaimer, the term of this patent is extended or adjusted under 35 U.S.C. 154(b) by 0 days.

(21) Appl. No.: 11/712,127

(22) Filed: Feb. 27, 2007

(65) Prior Publication Data

US 2008/0209601 P1 Aug. 28, 2008

(51) Int. Cl.
*A01H 5/00* (2006.01)

(52) U.S. Cl. ..... Plt./161

(58) Field of Classification Search ..... Plt./161
See application file for complete search history.

*Primary Examiner*—Kent L. Bell
*Assistant Examiner*—June Hwu
(74) *Attorney, Agent, or Firm*—Wells St. John P.S.

(57) ABSTRACT

A new and distinct variety of apple tree Malus pumila Mill, and which is denominated varietally as 'PB-148' and which produces an attractively colored apple which is mature for harvesting and shipment about August 30$^{th}$ under the ecological conditions prevailing near Ephrata, Wash.

4 Drawing Sheets

BACKGROUND OF THE NEW VARIETY

The present invention relates to a new and distinct variety of apple tree *Malus pumila Mill* and which has been denominated varietally as 'PB-148'; and more specifically to an apple tree which is principally characterized as to novelty by bearing an attractive, highly colored apple having a good flavor, and shelf life and which is ripe for harvesting and shipment under the prevailing ecological conditions existing in the Columbia Basin area of central Washington State on and about August 30$^{th}$.

The present variety of apple tree *Malus pumila Mill* resulted from a cross pollination which was made by me of a 'Gala' apple tree (U.S. Plant Pat. No. 3,637) with a New Zealand Red Crab Apple Tree, which is denominated varietally as 'Jack Humm' and which is unpatented. The variety 'Jack Humm' was derived from a cross of the unpatented Crab Apple Tree 'Gorgeous' and the unpatented variety 'John Downie.' The variety 'John Downie' is known for producing fruit which are excellent for jelly making. This cross-pollination occurred within the cultivated area of my orchard which is located in Central Otago, New Zealand during the 1987 growing season. After observing the characteristics of this new tree for a number of years, budwood from the new 'PB-148' apple tree, then growing in Central Otago, New Zealand, was sent to the quarantine facility which is located at Prosser, Wash. in August of 2000. Following the treatment of the budwood by the Prosser facility, virus-free budwood was then released from the facility in August, 2001. Thereafter, this novel tree was asexually reproduced using this same budwood by grafting this same budwood into test trees which were then growing on 'M26' rootstock (unpatented) at a commercial test orchard which was located near Ephrata, Wash. Thereafter, the second generation grafted trees, which were growing in Ephrata, Wash. were observed for three cropping seasons and the fruit produced from same was repeatedly compared and contrasted with the fruit earlier produced on the original mother tree which was still growing in my orchard which is located in Central Otago, New Zealand. These subsequent botanical and pomological comparisons of the fruit produced by the second generation trees with that of the original mother tree revealed that the second generation grafted trees produced fruit, and had other botanical characteristics which appeared to be identical to that displayed by the original mother tree.

SUMMARY OF THE NEW VARIETY

The 'PB-148' apple tree is characterized principally as to novelty by producing an attractive, highly colored fruit which is ripe for harvesting and shipment about August 30$^{th}$ under the ecological conditions prevailing in the Columbia Basin area of central Washington State. The present variety is easily distinguishable from the fruit produced by 'Gala' apple trees (U.S. Plant Pat. No. 3,637) in view of its attractively colored fruit. In relative comparison to the 'Gala' apple trees grown in the same geographical location, the average harvesting date for the most common 'Gala' cultivars grown in the same geographical is about the same. However, the shape of the new variety of apple is considered round in contrast to the apples produced by the 'Gala' apple tree which appears more conically shaped. In relative comparison to the New Zealand Red Crab Apple Tree 'Jack Humm' which was crossed with a 'Gala' apple tree in order to produce the mother three 'PB-148', the present variety is clearly distinguishable by producing fruit which has a larger size and a noteworthy color. In this regard, the 'Jack Humm' Crab Apple Tree typically produces clusters of oblong fruit having a bright crimson-red skin which has a yellow-orange underside. The fruit of the 'Jack Humm' typically has a length of about 40 mm, and further persists on the tree long after the leaves have left the tree and often into the winter.

BRIEF DESCRIPTION OF THE DRAWINGS

The accompanying drawings are color photographs of various aspects of the present plant. The colors are as nearly true as is reasonably possible in color representations of this type. Due to chemical development, processing and printing, the leaves and fruit of the present variety may or may not be accurate when compared to the actual specimen. For this reason, future color reference should be made to the color plates as provided by the Royal Horticultural Society, London, and other general color descriptions as provided for, hereinafter.

NOT A COMMERCIAL WARRANTY

The following detailed description has been prepared to solely comply with the provisions of 35 U.S.C. § 112, and does not constitute a commercial warranty, (either expressed or implied), that the present variety will, in the future, display the botanical, pomological or other characteristics as set forth, hereinafter. Therefore, this disclosure may not be relied upon to support any future legal claims including, but not limited to, breach of warranty of merchantability, or fitness for any particular purpose which is directed, in whole, or in part, to the present variety.

DETAILED DESCRIPTION

Referring more specifically to the pommological and botanical details of this new and distinct variety of apple tree, the following has been observed during the 2005 growing season under the ecological conditions prevailing in a test orchard which is located near Ephrata, Wash. All major color code designations are by reference to The Royal Horticulture Society Colour Chart (3$^{rd}$ Edition) provided by the Royal Horticulture Society of Great Britain.

Tree:

*Size.*—Generally — Average as compared to other apple cultivars. The second generation trees growing at the orchard near Ephrata, Wash. and which were grafted with the budwood coming from the original mother tree in 2001 now have a height of about 3.7 meters; and a width of about 1.2 meters. The trees were 6 years old when observed.

*Vigor.*—The present variety is considered vigorous under the current ecological conditions prevailing near Ephrata, Wash.

*Hardiness.*—Generally — Considered hardy under the ecological conditions prevailing in Ephrata, Wash.

*Productivity.*—Generally — Considered average.

*Regularity of bearing.*—Considered regular.

Trunk:

*Size.*—The average diameter of the trunk when measured at a distance of about 45 cm. above the surface of the earth is about 8 cm.

*Bark texture.*—Generally — Considered average in smoothness.

*Bark color.*—Grey-orange (RHS 177A).

*Bark lenticels.*—Numbers — Considered numerous, and generally horizontal to the plane.

*Bark lenticels.*—Length — About 2.5 mm. to about 4 mm.

*Bark lenticels.*—Width — About 1.5 mm.

*Bark lenticels.*—Color — Considered white (RHS N155D).

Branches:

*Numbers.*—First year branches are considered moderate in number and generally have no spur development. Likewise, scaffold branches are also considered moderate in number as compared to other varieties.

Figure 1:
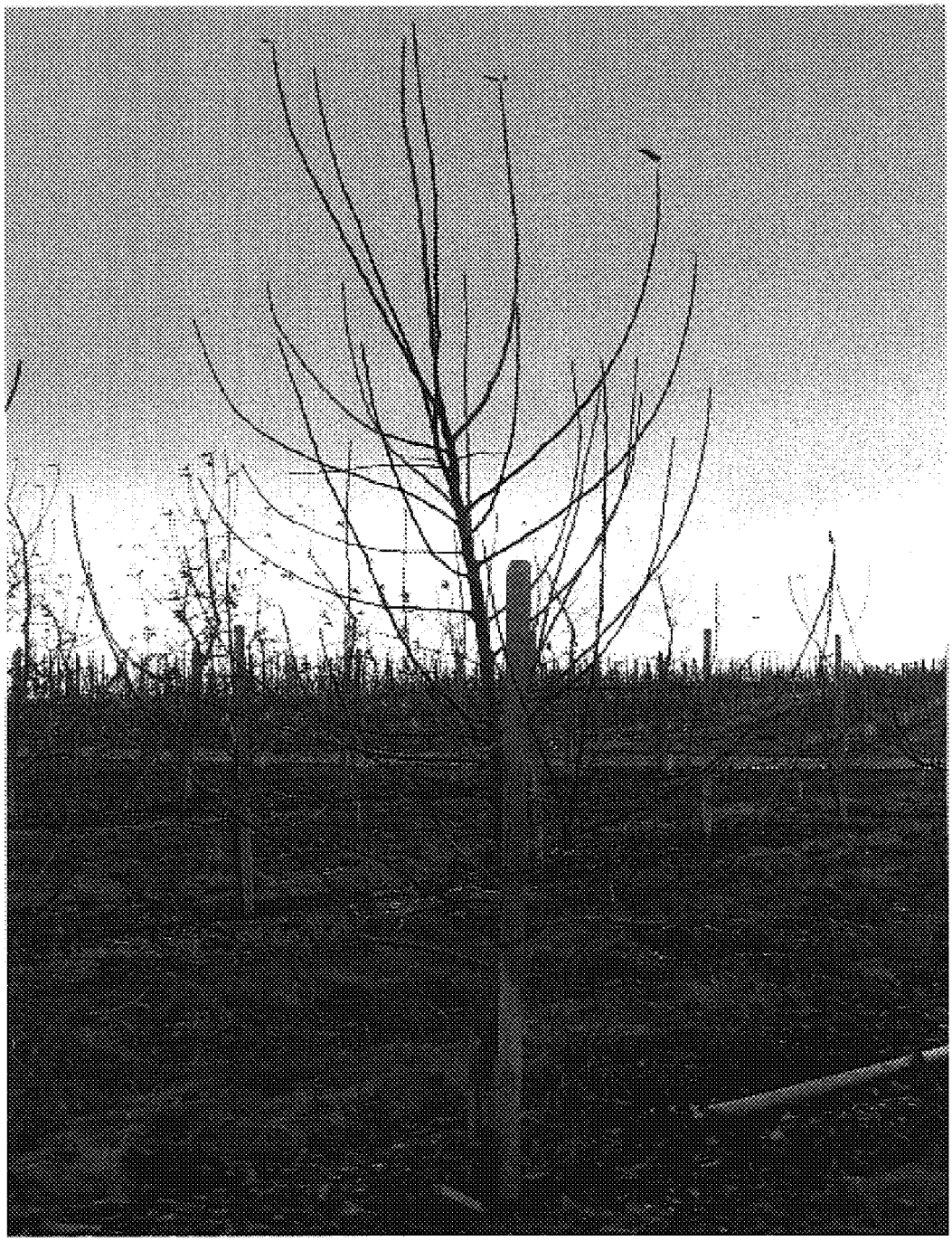
FIG. 1 shows the growing habit of a second generation tree of the variety 'PB-148' as grown on 'M26' rootstock (unpatented) at an orchard which is located near Ephrata, Wash.
Figure 2:
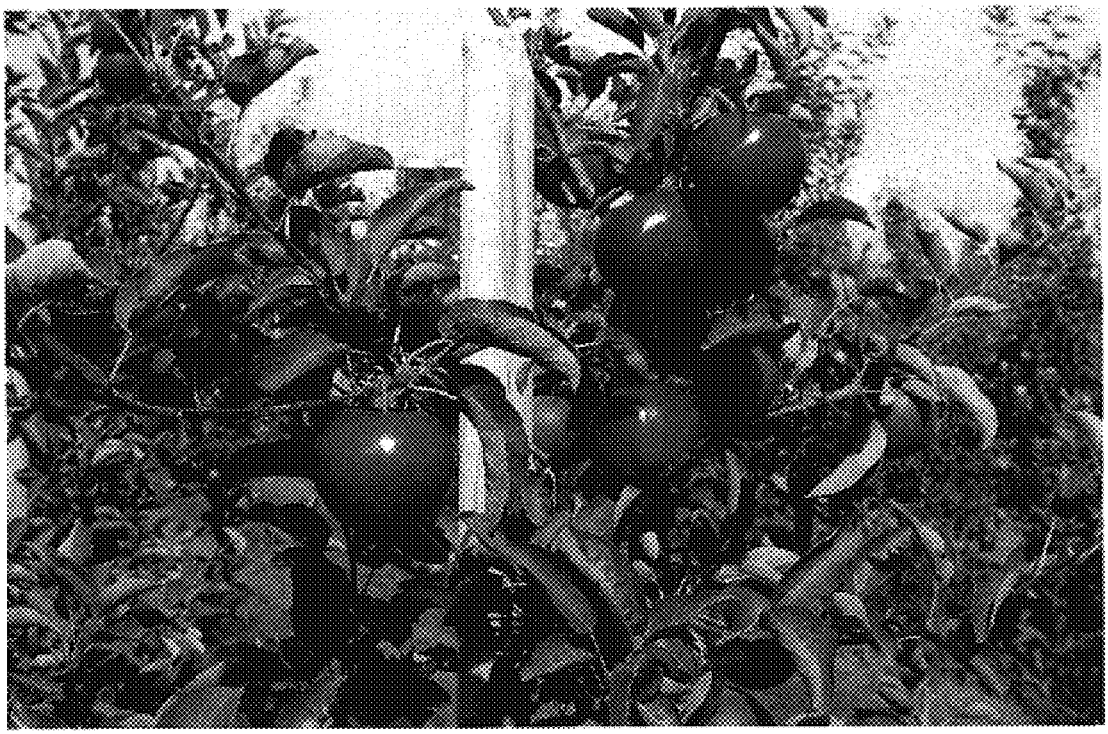
FIG. 2 is a photograph of the highly colored and attractive fruit produced by the 'PB-148' apple tree when grown on the same second generation trees which are growing at the same orchard which is located near Ephrata, Wash.
Figure 3:
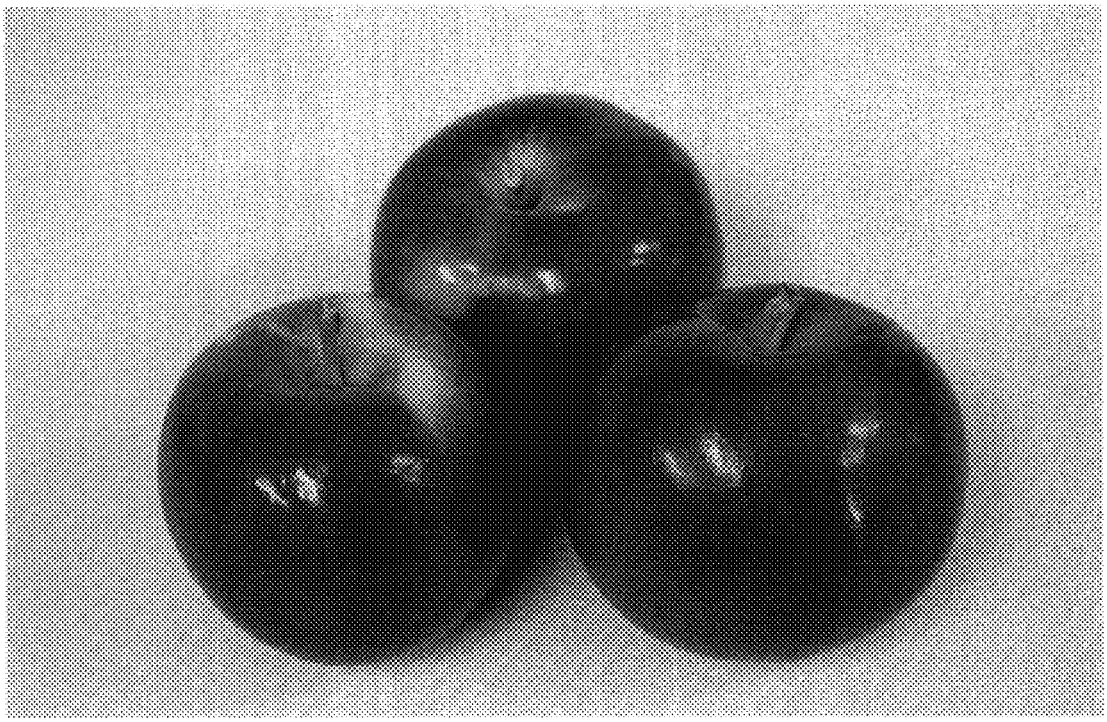
FIG. 3 is a photograph which exhibits the highly colored, and attractive fruit produced from the second generation trees of 'PB-148' now growing on 'M26' rootstock at the orchard which is located near Ephrata, Wash.
Figure 4:
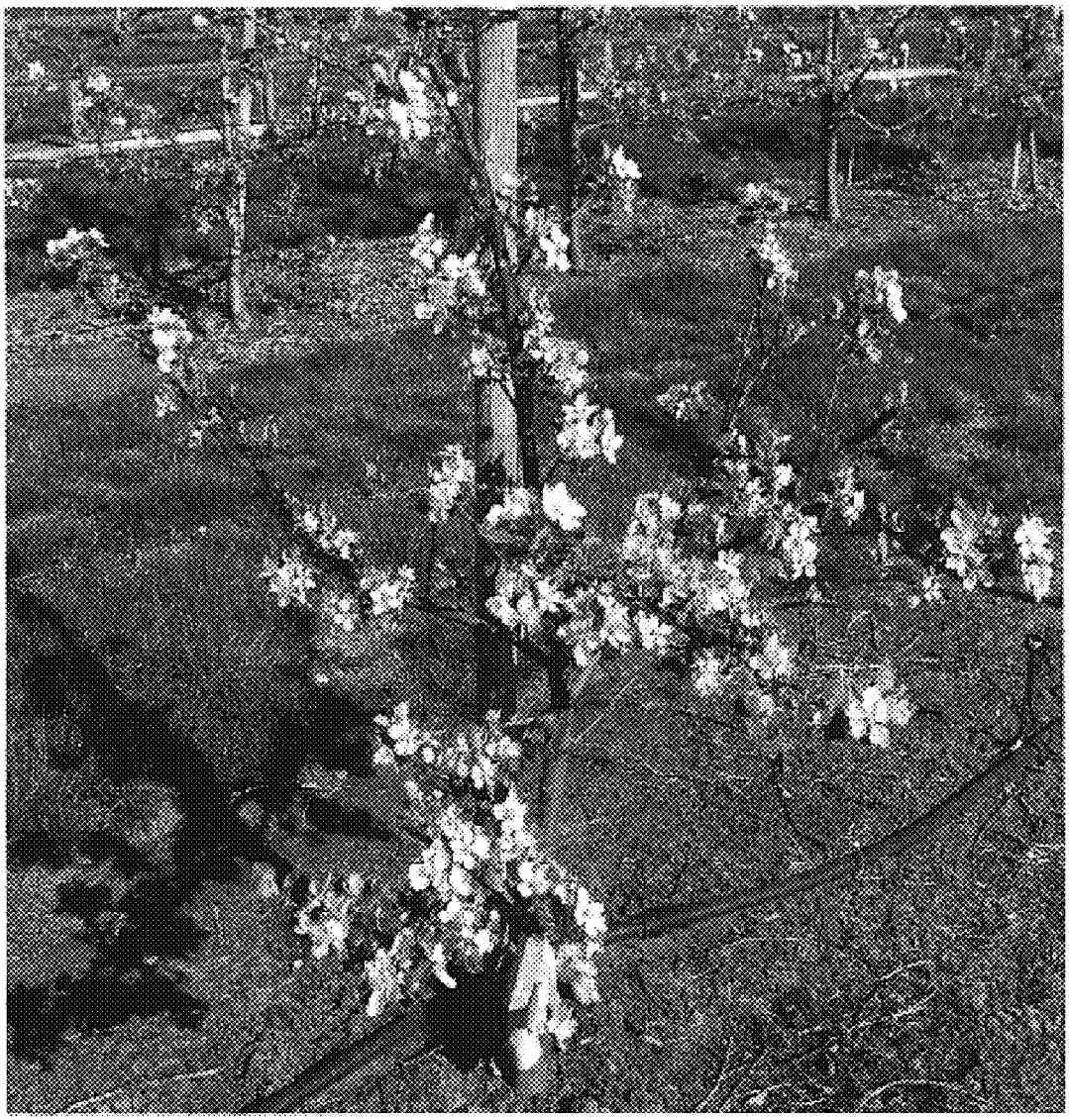
FIG. 4 is a photograph displaying the blooming characteristics of second generation 'PB-148' apple trees now growing on 'M26' rootstock (unpatented) at an orchard which is located near Ephrata, Wash.
Figure 5:
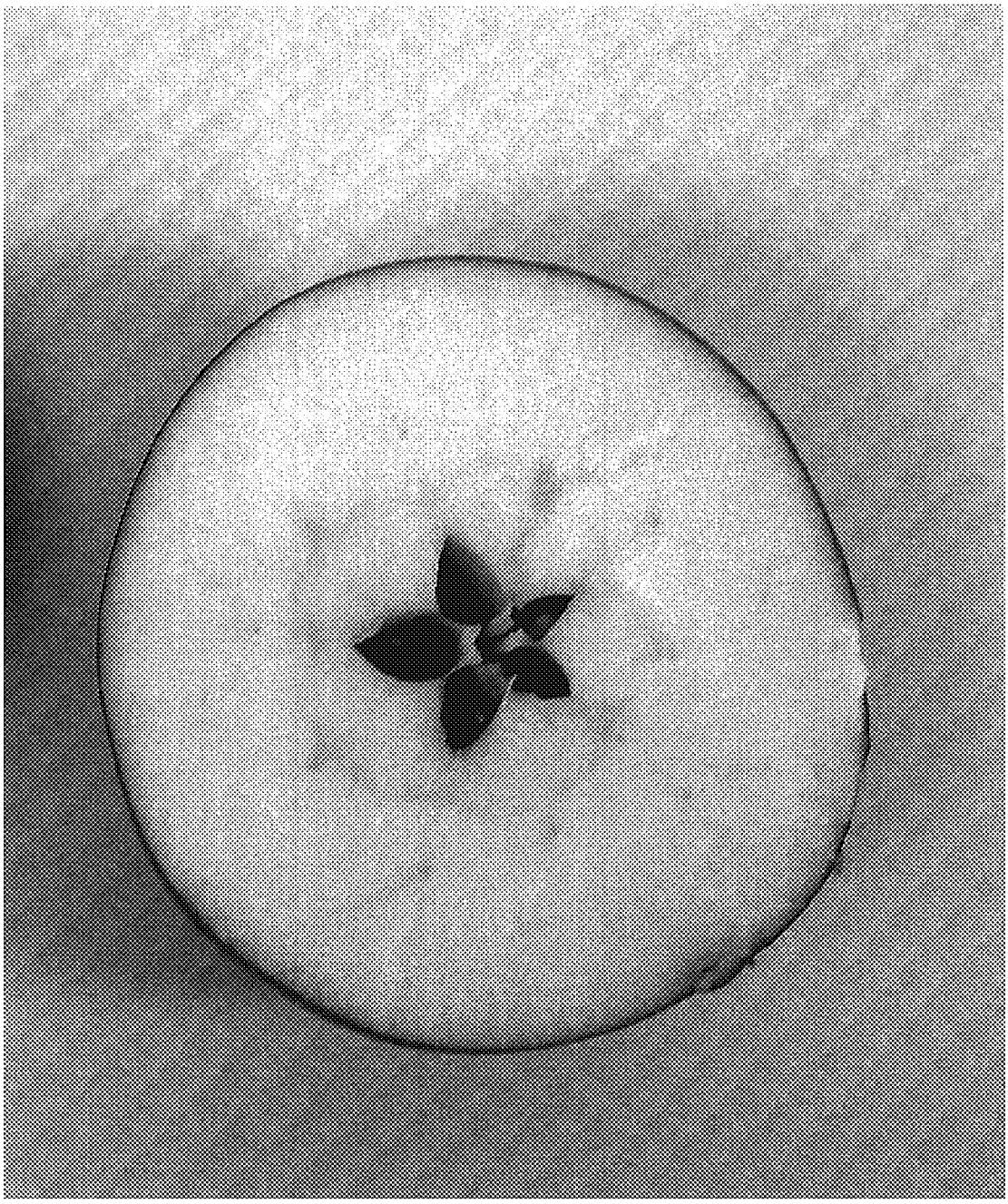
FIG. 5 is a photograph which depicts the flesh characteristics of the fruit produced by the new variety of apple tree.

*Crotch angle.*—First year branches have a crotch angle of about 55 degrees to about 90 degrees. Scaffold branches have a crotch angle of about 60 degrees to about 90 degrees. This characteristic is seen, at least in part, by a study of FIG. 1.

*Bark color.*—First year branches have a purple bark color (RHS N77B). In contrast, scaffold branches have a bark color considered to be grey-purple (RHS 187A).

*Bark lenticels.*—First year branches — Present and round to slightly elongated in shape. The lenticels have a length of about 1 to about 1.5 mm.; and a width of about 1 mm. These bark lenticels are tangentially oriented.

*Bark lenticels.*—First year wood — The color of the bark lenticels are considered white. This color is not considered distinctive of the variety, however.

*Bark lenticels.*—Scaffold branches — The bark lenticels on the scaffold branches are numerous and oriented substantially horizontal to plane. These bark lenticels have a length dimension of about 1.5 to 3 mm. and a width dimension of about 1.5 mm.

*Bark lenticel color.*—Scaffold branches — The color of the bark lenticels is considered white (RHS N155D).

*Branch pubescence.*—First year wood — Present, considered moderate in amount, and white in color. This color is not distinctive of the variety, however.

*Internodes.*—Spacing — On first year wood the average spacing is about 5.1 cm.

*Fruit spur development.*—Scaffold branches — Considered moderate in amount and generally developing on two and three year old wood.

Leaves:

*Surface texture.*—Considered glabrous, leathery and having a glossy sheen.

*Pubescence.*—Generally — May be considered abundant on the dorsal surface of the leaf.

*Pubescence color.*—Considered white. This color is not distinctive of the variety, however.

*Average leaf length.*—About 9.5 cm.

*Average leaf width.*—About 6.9 cm.

*Petiole.*—Size — Considered average for the variety.

*Petiole.*—Length — About 2.4 cm.

*Petiole.*—Width — As measured at about mid-point along the petiole, about 2 mm.

*Leaf form.*—Considered oval.

*Marginal form.*—Considered mostly serrate, although some double serrate marginal leaf forms may be found.

*Leaf tip.*—Shape — Considered broadly acute.

*Leaf stipules.*—Generally — Normally present, and having a length dimension of about 10 to 15 mm.; and a width dimension of about 2 to about 6 mm. Leaf Stipules — Color — Yellow-green (RHS 146C).

*Leaf color.*—Dorsal surface — Yellow-green (RHS 146A).

*Leaf color.*—Ventral surface — Yellow-green (RHS 146C).

Flowers:

*Time to bloom.*—Typically about Apr. 29, 2006 under the prevailing ecological conditions existing near Ephrata, Wash.

*Flower size.*—Generally — Considered medium for the variety, and having an average diameter of about 45 mm. Flower Petal Arrangement — Intermediate.

*Petal size.*—Width — About 16.5 mm.

*Petal size.*—Length — About 20.3 mm.

*Petal color.*—Considered white (RHS N155B); and further having highlights from the red-purple group (RHS 67A).

*Stamen.*—Length — In a range of about 5 to 10 mm, with an average length of about 7.2 mm.

*Stamen.*—Color — Considered yellow (RHS 6D).

*Anthers.*—Color — At full maturity, the anthers have a yellow color (RHS 5D).

*Anthers.*—Length — About 2.7 mm.

*Pistil length.*—About 14.3 mm.

*Pistil color.*—Yellow (RHS 6D).

*Styles.*—Numbers — 5.

*Styles.*—Form — The styles are typically fused at the base and the base is pubescent.

*Styles.*—Length — About 10.2 mm.

*Stigma.*—Shape — Generally having a rounded top.

*Sepals.*—Form — Curled downwardly and inwardly.

*Sepals.*—Length — About 7.3 mm.

*Sepal pubescence.*—Present, on both the dorsal and ventral surfaces but it is considered colorless.

*Sepal.*—Color — considered yellow-green (RHS 143B); and having highlighted tips from the red group (RHS 53A).

Fruit:

*Maturity when described.*—Generally the fruit produced by the present variety is described as it would be found at full commercial maturity. In this regard, the fruit of the present variety was ripe for commercial harvesting and shipment under the ecological conditions prevailing near Ephrata, Wash. on Aug. 30, 2005. The harvesting date of the present variety is considered to be similar to the 'Gala' apple tree cultivars growing in the same geographical region.

*Fruit size.*—Considered average for the species, and having an average diameter of about 8.1 cm.

*Fruit form.*—Considered round.

*Fruit stem.*—Generally — Considered short and medium stout for the species. The stem has an average length of about 1.5 cm.

*Stem cavity.*—Average width — About 33.4 mm.

*Stem cavity.*—Average depth — About 16.6 mm.

*Basin cavity.*—Average width — About 27.5 mm.

*Basin cavity.*—Average depth — About 9 mm. Some slight ribbing is evident with the basin cavity.

*Calyx.*—Generally — The eye is generally connivent, and some aspects of the eye is divergent.

*Fruit skin.*—Texture — Considered glabrous and a bloom is present.

*Fruit skin appearance.*—Having a highly attractive blush with an indistinct mottled stripe. The overcolor of the fruit, that is the stripe, is selected from the red group (RHS 46A to 46B, respectively). The undercolor of the fruit, that is the blush, is selected from the yellow group (RHS 2B).

*Lenticels.*—Generally — Normally present and moderate in number. They are indistinct and not particularly distinctive of the present variety.

*Core.*—Generally — The core line attachment is considered basal clasping.

*Core.*—Position — Considered medium for the variety.

*Locule shape.*—Considered round and not tufted.

*Tube.*—Shape — Considered cone shaped.

*Sepals.*—surface texture — Considered downy.

*Stamen position.*—Generally — Considered basal.

*Locules.*—Generally — Asymmetrically abaxile and open.

*Seeds.*—Numbers — 2 to 3 seeds per locule are found.

*Seeds.*—Color — Grey-orange (RHS 175A).

*Seeds.*—Shape — Generally considered acuminate. The seeds have an average diameter of about 4 mm.; and an average length dimension of about 9 mm.

*Flesh color.*—White. This flesh color is not distinctive of the present variety.

*Flesh firmness.*—Generally — Considered firm and crisp for the species. Flesh texture is considered fine.

*Flesh flavor.*—Considered sprightly, and sub-acid to mildly acidic.

*Brix.*—At full commercial maturity about 12.9.

*Fruit firmness.*—Considered — 18.1 pounds at full commercial maturity.

*Starch content.*—Based upon a scale of 1–6, and wherein 1 is considered to have a high starch content, and 6 is considered to have no starch, the present variety is considered a 1.8.

*Fruit aroma.*—Considered slightly aromatic and sometimes wanting.

*Keeping quality.*—The present variety has been kept up to 3 months under typical apple storage conditions with no deleterious effects noted.

*Pollination requirements.*—The present variety may be pollinated by any diploid apple tree blooming at about the same blooming season.

*Fruit use.*—Primarily for fresh eating for both local and long distance markets.

*Disease and insect resistance.*—The present variety is considered susceptible to all insects and diseases found in the region of Central Washington.

Although the new variety of apple tree possesses the described characteristics when grown under the ecological conditions prevailing near Ephrata, Wash., in the south central portion of Washington state, it should be understood that variations of the usual magnitude and characteristics incident to changes in growing conditions, fertilizing, pruning, pest control, and horticultural management practices are to be expected.

Having thus described and illustrated my new variety of apple tree, what I claim is new, and desire to secure by Plant Letters Patent is:

1. A new and distinct variety of apple tree *Malus pumila Mill* substantially as illustrated, and described, and which is characterized principally as to novelty by bearing an attractively colored apple which is mature for harvesting and shipment about August $30^{th}$ under the ecological conditions prevailing near Ephrata, Wash.

* * * * *